United States Patent
Shoji

(10) Patent No.: US 7,058,518 B2
(45) Date of Patent: Jun. 6, 2006

(54) GAS SENSOR, FUEL CELL SYSTEM THEREWITH, AND AUTOMOBILE THEREWITH

(75) Inventor: Rihito Shoji, Kadoma (JP)

(73) Assignee: Matsushita Electric Industrial Co., Ltd. (JP)

( * ) Notice: Subject to any disclaimer, the term of this patent is extended or adjusted under 35 U.S.C. 154(b) by 56 days.

(21) Appl. No.: 10/515,863

(22) PCT Filed: May 18, 2004

(86) PCT No.: PCT/JP2004/007030
§ 371 (c)(1),
(2), (4) Date: Nov. 24, 2004

(87) PCT Pub. No.: WO2004/106909
PCT Pub. Date: Dec. 9, 2004

(65) Prior Publication Data
US 2005/0228596 A1 Oct. 13, 2005

(30) Foreign Application Priority Data
May 29, 2003 (JP) ............................. 2003-152489

(51) Int. Cl.
*G01N 31/00* (2006.01)
*G06F 19/00* (2006.01)
(52) U.S. Cl. ........................................................ 702/24
(58) Field of Classification Search .................. None
See application file for complete search history.

(56) References Cited
U.S. PATENT DOCUMENTS
5,366,821 A * 11/1994 Merritt et al. ............... 429/21
6,468,681 B1 * 10/2002 Horiguchi .................... 429/26

FOREIGN PATENT DOCUMENTS

| JP | 58-14045 A | 1/1983 |
|----|----|----|
| JP | 6-223850 A | 8/1994 |
| JP | 7-55748 A | 3/1995 |
| JP | 8-50109 A | 2/1996 |
| JP | 8-101156 A | 4/1996 |
| JP | 8-184576 A | 7/1996 |
| JP | 9-5277 A | 1/1997 |
| JP | 2003-98147 A | 4/2003 |

* cited by examiner

Primary Examiner—Bryan Bui
Assistant Examiner—Aditya S. Bhat
(74) Attorney, Agent, or Firm—Rossi, Kimms & McDowell, LLP

(57) ABSTRACT

The gas sensor passes at least three levels of current through the heater element, stepwise and continuously for a predetermined time. The calculator loads voltages across the heater element for respective current values after a predetermined elapsed time, to obtain temperature from a voltage across the heater element, for the minimum amount of current. Further, from the temperature, zero-point correcting formulas, and sensitivity correcting formulas, the calculator corrects the voltages across the heater element to obtain respective normalized outputs. From the difference between these normalized outputs, the calculator obtains humidity to correct at least one of the normalized outputs with the humidity and the humidity correcting formula. In such a way, the calculator obtains the concentration of the gas to be sensed.

25 Claims, 12 Drawing Sheets

GAS SENSOR, FUEL CELL SYSTEM THEREWITH, AND AUTOMOBILE THEREWITH

This application is a U.S. national phase application of PCT international application PCT/JP2004/007030.

TECHNICAL FIELD

The present invention relates to a gas sensor for sensing the concentration of a gas to be sensed and humidity, mixed in atmospheric air containing moisture. The present invention also relates to a fuel cell system using the gas sensor, and to an automobile using the system.

BACKGROUND ART

Fuel cells, expected as a bargaining chip to solve energy and environmental issues, have been positively developed in recent years. Especially, a fuel cell with a solid polymer film used as its electrolyte is easy to handle owing to its low operating temperature of approximately 80° C., and thus is currently a mainstream in development of fuel cells. However, in such a type of fuel cell, where hydrogen is used as a fuel, a gas sensor for sensing hydrogen is required as a safety measure against leakage.

A conventional gas sensor senses the change in heat conductivity due to the presence of hydrogen, as the change in temperature of a heater element, using a property of hydrogen that is its heat conductivity is extremely high compared to other gases. For example, if hydrogen exists in the air, more heat is lost from the heater element than in a case where hydrogen does not exist. Consequently, the temperature of the heater element changes according to the hydrogen concentration. The conventional gas sensor electrically senses this temperature change as the change in resistance value of the temperature-sensing element.

The gas sensor uses a platinum thin-film resistive element for the heater element (also used for a temperature-sensing element). This element, a thin-film, can be manufactured using semiconductor fine processing technology (i.e. micromachining), enabling a submicroscopic heater element to be formed. Accordingly, the response speed of the gas sensor is enhanced with lower power consumption. Such a gas sensor is disclosed in Japanese Patent Unexamined Publication No. 8-101156, for example.

When such a gas sensor is used to sense hydrogen leakage, moisture in hydrogen, which is a gas to be sensed, causes a problem. That is, if moisture does not exist, the resistance value of the heater element changes according to the hydrogen concentration. Meanwhile, if moisture exists, the resistance value changes according to the humidity also. Therefore, it is not possible to distinguish the change if it is due to hydrogen and/or moisture.

Consequently, the conventional gas sensor changes the current passing through the heater element. This changes the output voltage across the heater element according to the degree of response. Then, the voltages across the heater element when different amounts of current are passed are substituted into an estimation equation obtained in advance, and then simultaneous equations are produced. Accordingly, the amount of each gas, namely the concentration of each gas is obtained from the solutions to the estimation equations.

Basically, such a solving method allows the gas concentrations of a plurality of components to be obtained. However, a problem exists where, at approximately 80° C., in such as sensing leakage from a fuel cell, hydrogen almost saturated with vapor leaks into the atmospheric air. If the change in heat conductivity of each of gas components is expressed with a linear expression as mentioned above, or if sensing is used only for a range where a linear expression well expresses, hydrogen concentration and humidity can be obtained using Chebyshev orthogonal polynomial. However, in the above-mentioned case, a large amount of vapor is assumed to exist as compared to hydrogen. Such a case shows a nonlinear (always having an order of two or more) characteristic. That is, the heat conductivity of the mixture once rises along with the humidity to a peak, and then falls. Therefore, just solving estimation equations simultaneously leads to troublesome calculation. Further, a plurality of solutions exist for humidity, and the humidity cannot be determined uniquely, thus neither can be the hydrogen concentration.

SUMMERY OF THE INVENTION

A gas sensor according to the present invention includes a heater element for contacting gas to be sensed, mixed in the atmospheric air containing moisture, a power supply unit for supplying the heater element with a current, and a voltmeter for measuring the voltage across the heater element. The gas sensor further includes a calculator for calculating and outputting humidity and concentration of the gas to be sensed from an output voltage of the voltmeter. The calculator supplies the heater element with at least three levels of current, stepwise and continuously for a predetermined time, using the power supply unit. Then, the calculator loads voltages across the heater element after a predetermined elapsed time for the respective current values, and calculates the temperature from the voltage across the heater element for the minimum amount of current. From the temperature, and from a zero-point correcting formula and a sensitivity-correcting formula, obtained in advance with the known concentration of the gas to be sensed, the calculator corrects the voltages across the heater element for other than the above-mentioned minimum current to obtain respective normalized outputs. From the difference in these normalized outputs, the calculator calculates humidity, and corrects at least one of the normalized outputs with the humidity and a humidity correcting formula obtained in advance with the known concentration of the gas to be sensed, to obtain the concentration of the gas to be sensed. In such a way, the gas sensor according to the present invention outputs humidity and the concentration of the gas to be sensed accurately.

DETAILED DESCRIPTION OF PREFERRED EMBODIMENTS

Figure 1:
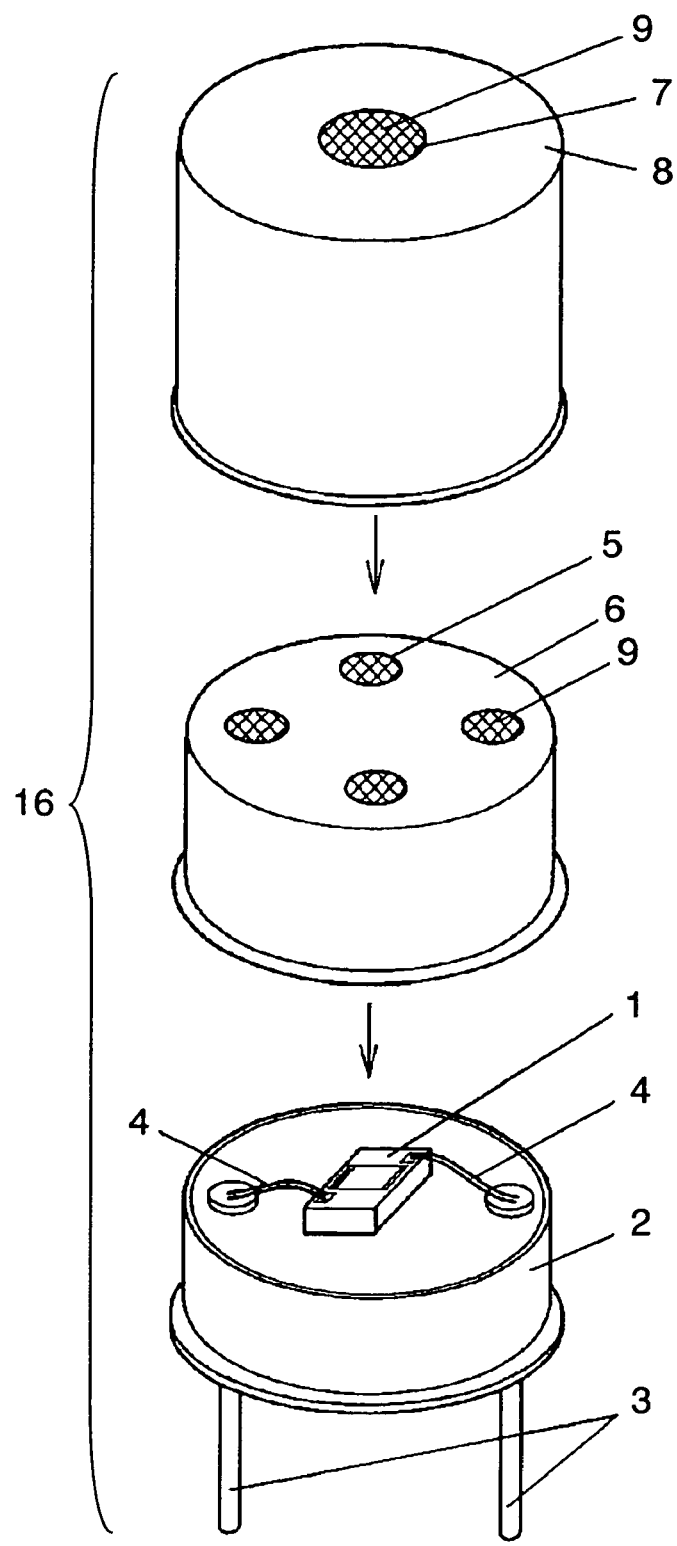
FIG. 1 is an exploded perspective view of a gas sensing part of a gas sensor of an embodiment according to the present invention.
Figure 2:
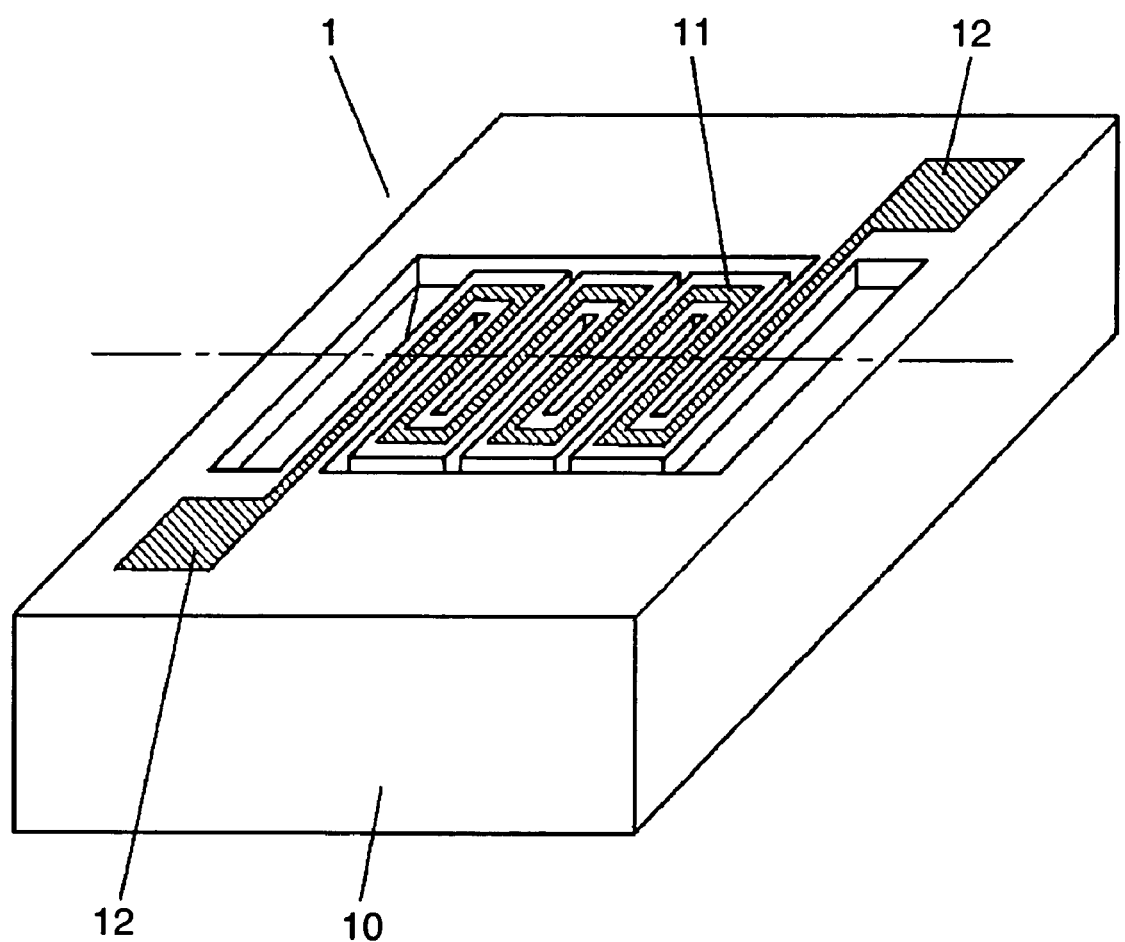
FIG. 2 is a schematic perspective view of a heater element of the gas sensor in FIG. 1.
Figure 3:
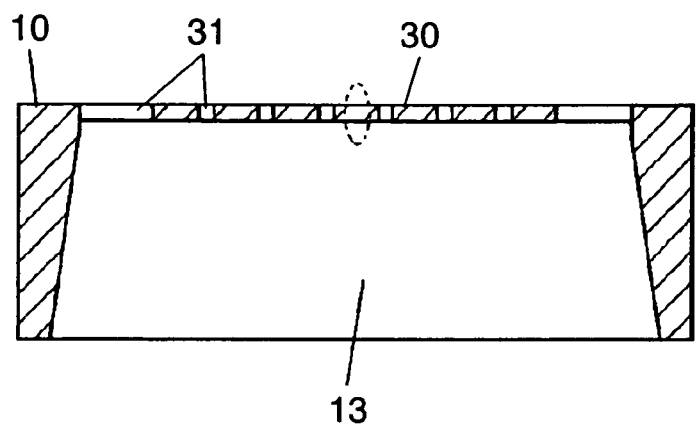
FIG. 3 is a schematic sectional view of the heater element in FIG. 2.
Figure 4:
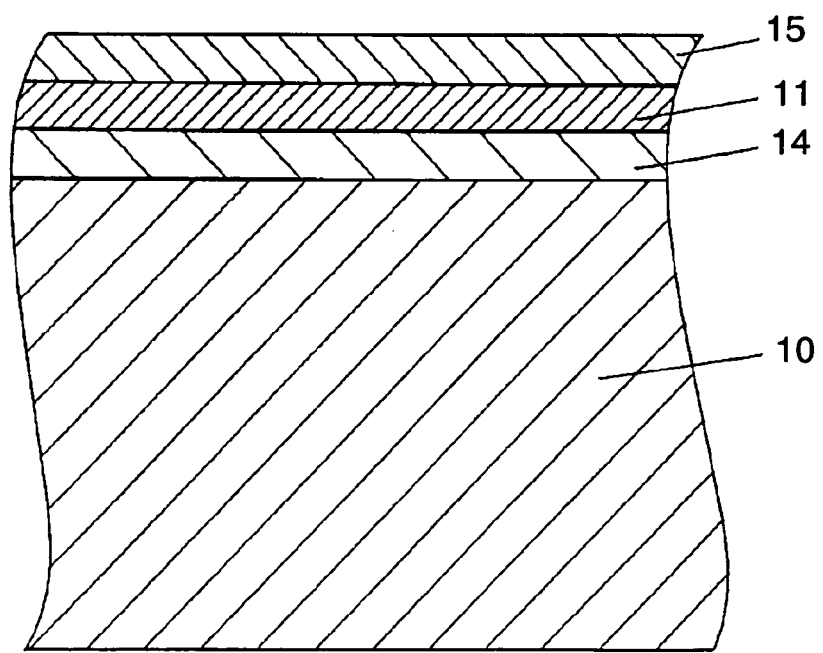
FIG. 4 is an enlarged sectional view of the heater element in FIG. 2.

Hereinafter, a description is made for an embodiment of the present invention using the drawings, where a gas to be sensed is assumed to be hydrogen. FIG. 1 is an exploded perspective view of a gas sensing part of a gas sensor of an embodiment according to the present invention. FIG. 2 is a schematic perspective view of a heater element of the gas sensor. FIG. 3 is a schematic sectional view of a part shown by the alternate long and short dashed line in FIG. 2. FIG. 4 shows an enlarged cross section of the winding part of heater element 1, shown by the area surround a broken line in FIG. 3. FIGS. 5A through 5E are schematic diagrams of an outline manufacturing process of the heater element. FIG. 6 is a schematic sectional view of the gas sensor.

Heater element 1, fixed on base 2, contacts a gas to be sensed and mixed in atmospheric air containing moisture. Two pins 3 are provided so as to pierce base 2, and each of two pairs of wires 4, made of gold, connects a top surface of each of pins 3 to heater element 1. Using a pair of wires 4 allows the gas sensor to be used continuously, improving reliability because one wire 4 remains connected even if another breaks. Base 2 has a double-canned makeup. That is, base 2 is capped with inner can 6 having four inner holes 5, and thereon further capped with outer can 8 having one outer hole 7. Inner holes 5 and outer hole 7 are displaced from each other when they are capped on base 2, not facing each other. Such positioning prevents a gas to be sensed to reach heater element 1 directly, reducing the impact on the output from the gas sensor due to the flow rate of a gas to be sensed. Base 2, inner can 6, and outer can 8 are all fixed each other with resistance welding. On inner holes 5 and outer hole 7, net 9 made of metal such as stainless-steel is fixed. Providing net 9 prevents flames from being propagated out of net 9, because the net absorbs the heat even if a gas to be sensed such as hydrogen burns inside the gas sensor. Net 9 works as long as it is provided on either inner holes 5 or outer hole 7. In addition, inner can 6, outer can 8, and net 9 are colored with black chromium plating. Such a manner allows cans 6 and 8, and net 9 to absorb radiation heat from heater element 1 and the outside, reducing the impact on the heating temperature of heater element 1, due to diffuse reflection on cans 6 and 8, and net 9. This works as long as any one of inner can 6, outer can 8, and net 9 is black-colored.

Heater element 1 includes pedestal 10, made of silicon; and heat generator 11, made of a platinum thin-film formed on pedestal 10 in a winding form with micromachining. Pedestal 10 is also processed in a winding form according to the shape of heat generator 11. In other words, winding part 30 is provided with heat generator 11. At both ends of heat generator 11, land 12 is provided for bonding wires 4. Still as shown in FIG. 4, heat generator 11 and land 12 are formed on insulating layer 14 made of silica. Also on the top surface of heat generator 11, protective layer 15 made of silica is formed. In this way, insulating layer 14, heat generator 11, and protective layer 15 make a laminated structure.

Forming protective layer 15 prevents an impure substance included in a gas to be sensed from directly adhering to the surface of heater element 1, improving the reliability of heater element 1. In addition, if insulating layer 14 and protective layer 15 are made of silica, they contact pedestal 10 made of silicon well firmly. This prevents an impure substance included in a gas to be sensed from directly adhering to the surface of heater element 1, improving the reliability of heater element 1. Moreover, making heat generator 11 with a platinum thin-film allows the wiring pattern of heater element 1 and heat generator 11 to be formed integrally, simplifying their manufacture process. In addition, heater element 1 with winding part 30 has a large surface area, improving the sensitivity of the gas sensor accordingly.

At winding part 30, dent 13 is formed under insulating layer 14, which is a dented part of the lower surface of pedestal 10 in FIG. 3, where heat generator 11 is provided. With such a construction, the heat capacity of heater element 1 is reduced, the gas sensor can respond in a high-speed, and is reduced in power consumption. Especially, if winding part 30, where dent 13 is provided, is made thin with a thickness of at least 3 micrometers but at most 10 micrometers, the heat capacity becomes extremely low, with the strength of heater element 1 being secured, reducing the time for temperature stabilization to the order of sub-second. In addition, at winding part 30, namely a part of heater element 1, through-hole 31 is provided. Through-hole 31 reduces the amount of heat transferring from heat generator 11 to pedestal 10, to reduce the time for stabilization of the element temperature, resulting in heater element 1 with an excellent reproducibility for repeated heating.

A description is made for an outline process for manufacturing such a heater element 1 with micromachining process using FIGS. 5A through 5E. Here, for easier understanding, the thicknesses of insulating layer 14 at winding part 30, heat generator 11, protective layer 15, and pedestal 10 are shown with exaggeration.

Figure 5A:
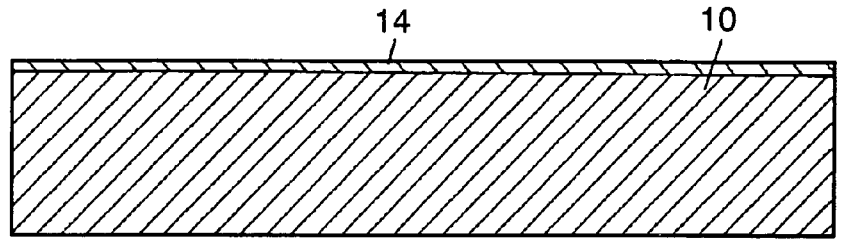
FIGS. 5A through 5E are sectional views showing an outline of a manufacturing process of the heater element in FIG. 2.
Figure 5B:
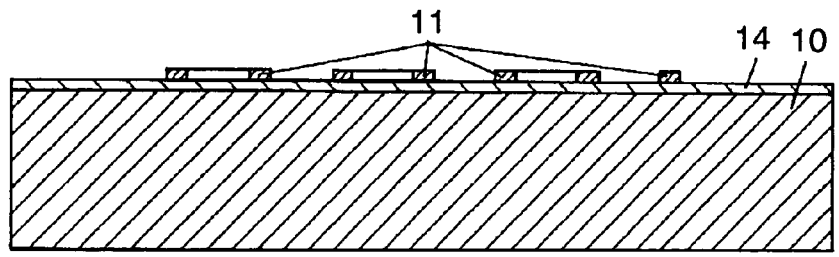
Figure 5C:
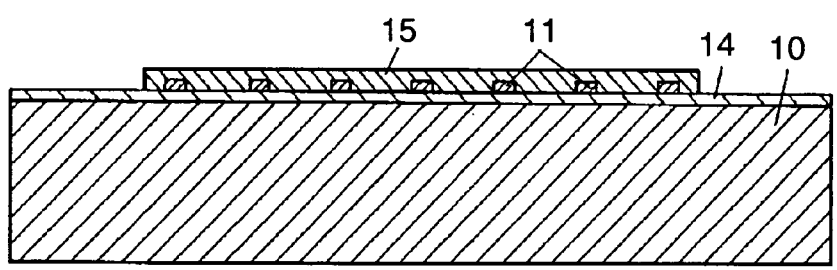
Figure 5D:
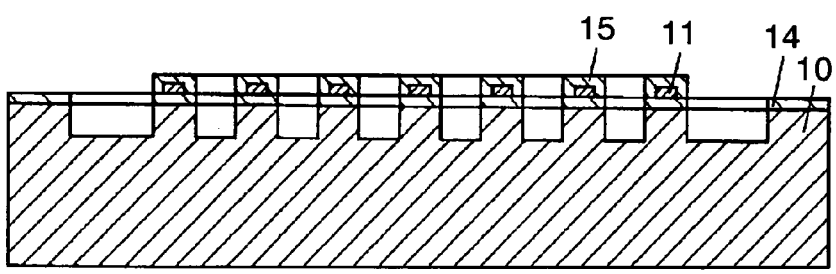
Figure 5E:
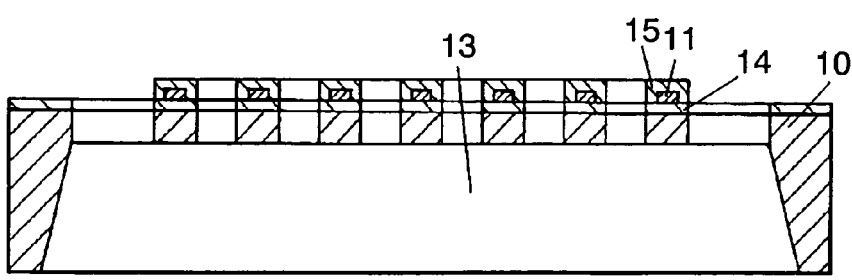
Figure 6:
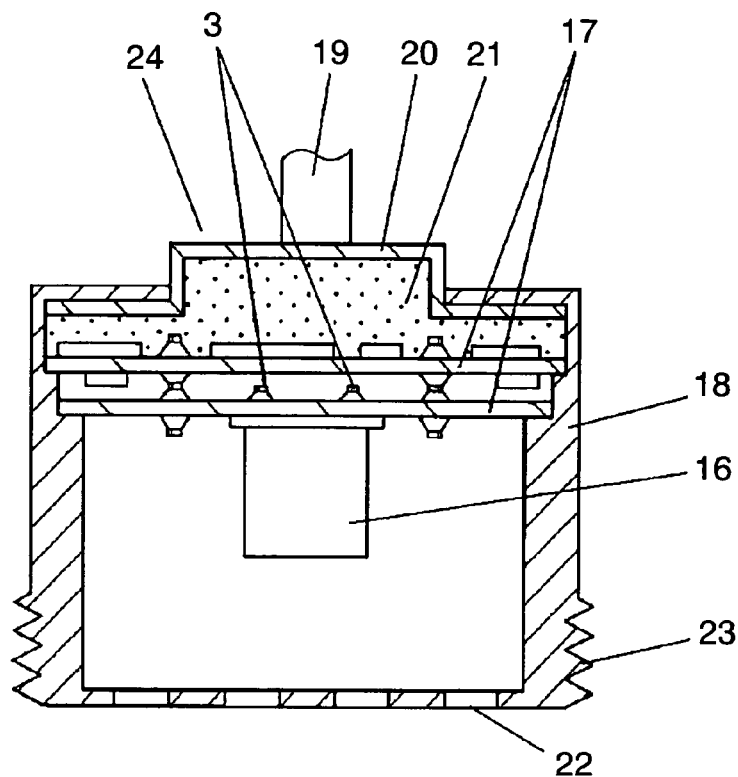
FIG. 6 is a schematic sectional view of the gas sensor of the embodiment according to the present invention.

First, as shown in FIG. 5A, form insulating layer 14 made of silica on the whole surface of pedestal 10 with sputtering. Next, as shown in FIG. 5B, sputter platinum using a mask pattern exposed in a winding form, on the top surface of insulating layer 14 to form heat generator 11. Further, as shown in FIG. 5C, form protective layer 15 made of silica with sputtering using a mask pattern exposed only at a part corresponding to heat generator 11. This causes protective layer 15 to be formed only on the top surface of heat generator 11. Next, as shown in FIG. 5D, deeply etch the silicon surrounding heat generator 11 using a winding-shaped pattern. Finally, as shown in FIG. 5E, shave pedestal 10 by etching the back surface of pedestal 10, namely the surface where heat generator 11 is not formed, to form dent 13. When dent 13 reaches the winding pattern previously dug, heater element 1 is formed with heat generator 11 as shown in FIG. 2, floating in the air in a winding shape.

Heater element 1 produced in such a way is packaged in a case composed of base 2, inner can 6, and outer can 8, shown in FIG. 1 to form sensing part 16. Sensing part 16 is connected to sensing circuit 17 electrically and mechanically, with pin 3 inserted into sensing circuit 17 and soldered as shown in FIG. 6. Sensing circuit 17 is inserted in container 18, and container lid 20 is inlaid with extraction cable 19 connected to sensing circuit 17, laced in advance. Moisture-resistant resin 21 is injected into the whole space which exists from the inlet (not illustrated) provided on container lid 20 and between sensing circuit 17 and container lid 20, and hardened. Container 18 and container lid 20 are crimped to each other after moisture-resistant resin 21 is injected and hardened.

Gas inlets 22 are provided on the bottom surface of container 18, and screw part 23 is processed for mounting a sensor on the side. In this way, gas sensor 24 completes.

Figure 7:
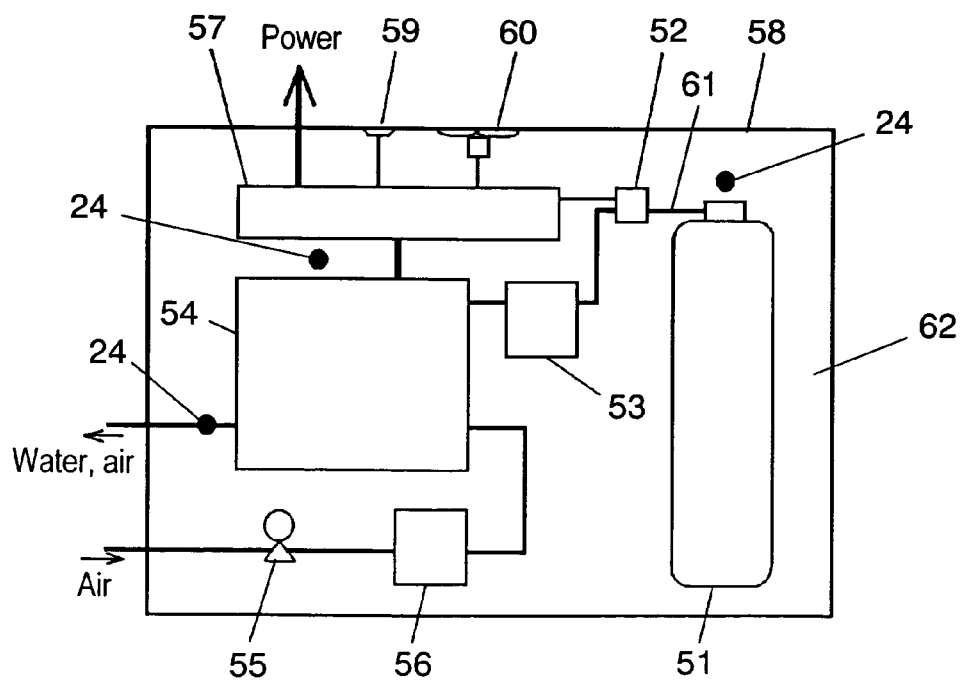
FIG. 7 is a schematic block diagram of a stationary fuel cell system on which the gas sensor of the embodiment according to the present invention installed.
Figure 8:
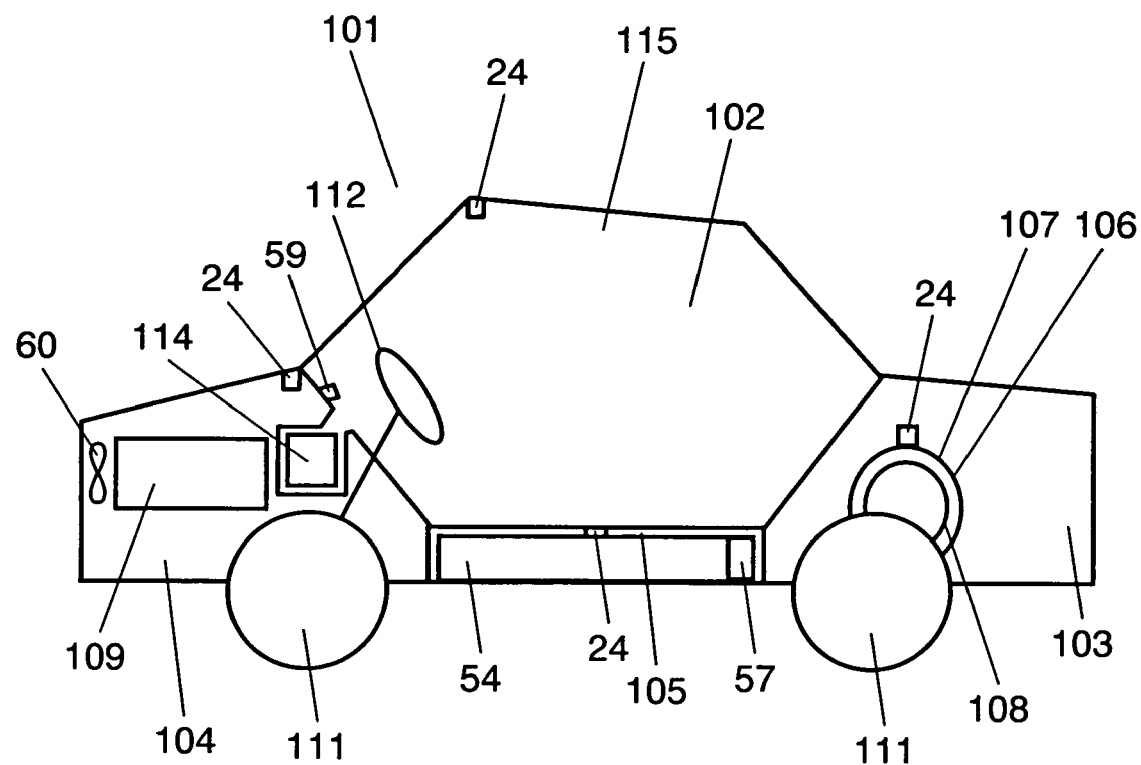
FIG. 8 is a sectional view showing an outline structure of an automobile equipped with the fuel cell using the gas sensor of the embodiment according to the present invention.

Next, a description is made for an example of mounting gas sensor 24 using FIGS. 7 and 8. FIG. 7 is a schematic block diagram of a stationary fuel cell system on which the gas sensor of the embodiment according to the present invention installed. FIG. 8 is a sectional view showing an outline structure of an automobile equipped with the fuel cell using the gas sensor of the embodiment according to the present invention.

First, a description is made for a stationary fuel cell system, taking the solid polymer film electrolyte type as an example, referring to FIG. 7. Fuel cell 54 generates electric power using hydrogen as a fuel. Hydrogen tank 51 is replaced with a reformer for a reforming-type fuel cell system. The hydrogen in hydrogen tank 51 is introduced to hydrogen humidifier 53 through isolation valve 52. Hydrogen is given moisture here to prevent the solid polymer film in the fuel cell from being dried. The humidified hydrogen is introduced to the hydrogen electrode of fuel cell 54. Meanwhile, air required to generate power, humidified with air humidifier 56, is introduced to the air electrode of fuel cell 54 with compressor 55. In this way, fuel cell 54 generates power and supply an external device with the power through control circuit 57 as shown by the heavy lines. In addition, the water resulting from the power generation is discharged to the outside with air from fuel cell 54.

The whole fuel cell system is contained in cabinet 58. In cabinet 58, gas sensors 24 for sensing hydrogen leakage are arranged near hydrogen tank 51, near fuel cell 54, at a part of the outlet piping for the air electrode of fuel cell 54, and at others. If any of gas sensors 24 senses hydrogen leakage, and its output exceeds a predetermined value, control circuit 57 closes isolation valve 52 to stop supplying fuel cell 54 with hydrogen. Then, alarm unit 59, which is an annunciator, and ventilation fan 60 are activated for ventilating space 62 including fuel cell 54 and duct 61 for hydrogen. Gas sensor 24, with the aforementioned makeup, is capable of sensing hydrogen concentration well accurately even in a gas to be sensed including moisture. Therefore, a fuel cell system with gas sensor 24 provides a high level of safety against hydrogen leakage. Still, instead of alarm unit 59, the annunciator may be composed of an indicator such as a red lamp.

Next, a fuel cell automobile is described using FIG. 8. Main body 101 of the automobile is formed with cabin space 102, hydrogen tank storage space 103, drive unit storage space 104, and underfloor space 105, each separately. Space 103 is equipped with tank 106 for storing hydrogen. Tank 106 is double-structured with outer tank 107 and inner tank 108, in order to secure safety especially against hydrogen leakage at the time of a crash, where inner tank 108 stores hydrogen therein. Drive unit storage space 104 is equipped with motor 109 for driving tire 111 supporting main body 101. Underfloor space 105 is equipped with fuel cell 54.

Using hydrogen supplied from tank 106 as a fuel, fuel cell 54 provided in underfloor space 105 generates power, and the power is supplied to motor 109 to drive tire 111. Here, the steering direction for tire 111 is controlled with steering wheel 112 in cabin space 102.

In such an automobile, the respective spaces are provided with gas sensors 24. Specifically, gas sensor 24 in cabin space 102 is provided at the front part of the ceiling, which is the highest part in cabin space 102. Gas sensor 24 in hydrogen tank storage space 103 is provided at the top of outer tank 107 because tank 106 is double-structured. Gas sensor 113 in drive unit storage space 104 is provided at the rear end of the hood (bonnet), which is the highest part in drive unit storage space 104. Gas sensor 113 provided in underfloor space 105 is arranged at the highest part of underfloor space 104. Further, although not illustrated, similarly to FIG. 7, the gas sensor is also arranged at a part of the outlet piping for the air electrode of fuel cell 54.

If any one of these gas sensors 24 senses hydrogen leakage, as described in FIG. 7, control circuit 57 blocks the hydrogen supply source to stop supplying fuel cell 54 with hydrogen. Further, alarm unit 59, which is an annunciator, alarms. In addition, ventilation fan 60 ventilates the space provided in main body 101. Still in FIG. 8, although ventilation fan 60 is provided only in space 104, similar fan(s) to ventilation fan 60 may be provided in other spaces.

In addition to the above, gas sensor 24 provided in cabin space 102 also senses moisture, and is usually used to control air conditioner 114 equipped at a part of cabin space 102 to keep optimum the humidity in cabin space 102. Using gas sensor 24 enables not only sensing hydrogen leakage, but obtaining humidity data. Consequently, gas sensor 24 usually controls the air conditioner, and when hydrogen leaks, it controls to ventilate and to block the hydrogen supply source, improving both safety and comfort of the automobile simultaneously.

Still, because hydrogen may leaks at any time, even while an automobile is not being used, gas sensors 24 are always operating. If any one of gas sensors 24 senses hydrogen leakage, ventilation fan 60 automatically ventilates to prevent hydrogen from pervading. In this case, heater element 1, with its very small size, needs very little electricity to work. Therefore, gas sensor 24 can be satisfactorily driven even while the automobile is not being used, and hydrogen leakage can be sensed even so, further improving safety.

Figure 9:
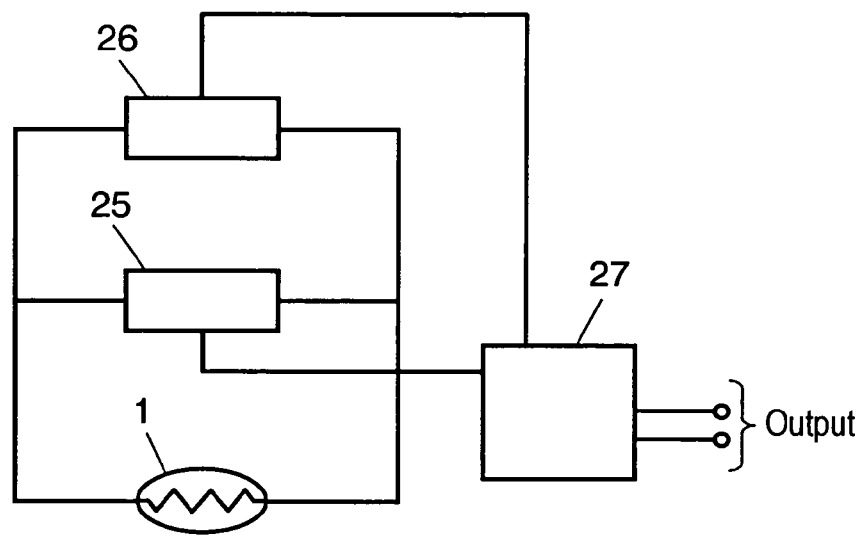
FIG. 9 is an outline circuit diagram of the gas sensor shown in FIG. 6.

Next, the operation of gas sensor 24 is described. FIG. 9 is an outline circuit diagram for illustrating the circuitry of a gas sensor according to the embodiment of the present invention. Heater element 1 is connected to constant current source 25 as a power supply unit, and also connected to voltmeter 26 for measuring a voltage across heater element 1, in parallel with constant current source 25. Constant current source 25 and voltmeter 26 are further connected to calculator 27 including a microprocessor. Calculator 27 controls constant current source 25, and also performs a predetermined calculation using the output from voltmeter 26 to output data of hydrogen concentration and humidity. Constant current source 25, voltmeter 26, and calculator 27 are included in sensing circuit 16 in FIG. 6.

Figure 10:
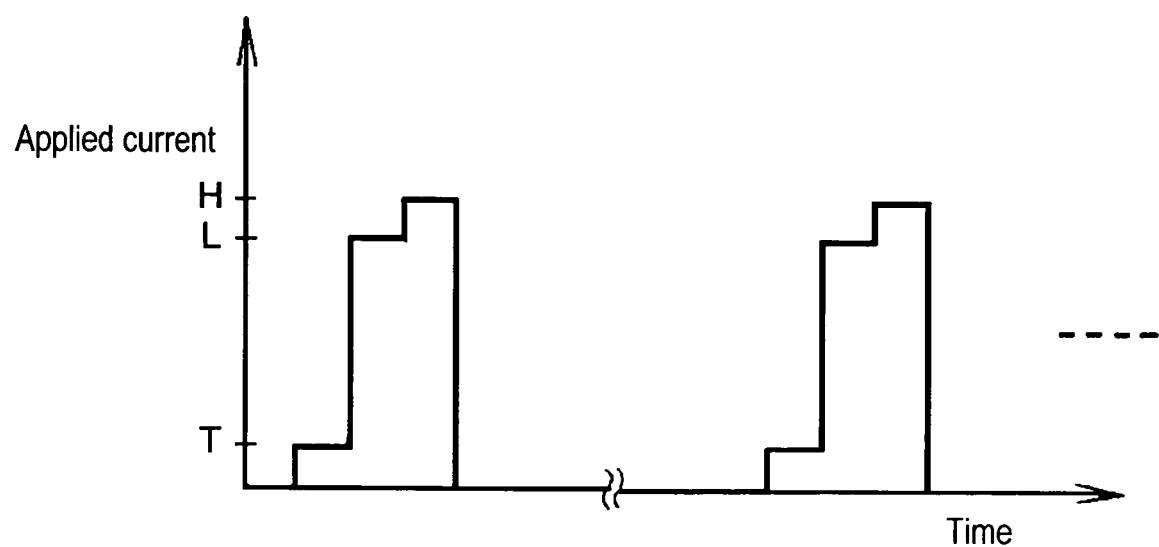
FIG. 10 is an outline waveform chart of current applied to the heater element in FIG. 2.

FIG. 10 is an outline waveform chart for the currents applied to heater element 1 of gas sensor 24. Constant current source 25 supplies heater element 1 with three levels of current, stepwise and continuously for a predetermined time, according to the instruction of calculator 27. Here, more than three levels of current may be supplied. In this embodiment, calculator 27 controls to supply current as follows: the first current value (first value) is 1 mA; second (second value), 7 mA; third (third value), 7.5 mA, for 0.1 second each. After completing of the supply of the third current, calculator 27 turns off the current to heater element 1 to wait 1.7 seconds. During this time, heater element 1 is cooled to the ambient temperature. Therefore, a current is applied with this operation repeated at an interval of one cycle per 2 seconds. Here, these current values and times are an example of the conditions obtained with heater element 1 in this embodiment, but the present invention is not limited to these values. Still, the current values of at least three levels passed through heater element 1 are desirably applied sequentially from low to high as in FIG. 10. This causes heater element 1 to be heated sequentially from at a low temperature to a high, reducing the possibility of destruction of element 1 resulting from a thermal shock due to rapid heating.

Calculator 27, with performing the above-mentioned current control, loads a voltage value from voltmeter 26 immediately before changing each current value, namely after such a predetermined elapsed time. Consequently, voltages of three points per one cycle are read. These voltages are assumed to be T value (first output), L value (second output), and H value (third output), from a low current to a high respectively.

Under a condition in which T value is obtained, the current value to heater element 1 is as small as 1 mA, and thus T value corresponds to a voltage of heater element 1 hardly heating, and a current value at which T value is obtained is within a range where heater element 1 hardly heats. In other words, the temperature of heater element 1 does not change with this current value. In this case, heater element 1 corresponds to a platinum temperature-sensing element, and thus T value of the voltage across element 1 is to represent roughly the ambient temperature of heater element 1 only, where the change in heat conduction depending on the kind of a gas is not sensed. In other words, under this condition, only the ambient temperature, with little gas sensitivity and humidity sensitivity, is sensed with a high accuracy.

L value and H value are voltages across heater element 1 at which heater element 1 heats. In those cases, voltages are obtained according to the temperature at which two kinds of heat balance: one is the heat lost from element 1 depending on the kind and concentration of a gas, and the ambient temperature; the other is the heat generated by element 1 itself. Therefore, L value and H value are voltages with parameters of an ambient temperature, and the kind and concentration of a gas combined. Still, heating temperature of heater element 1 for L value, with a small current passed through, is naturally lower than that for H value.

Figure 11:
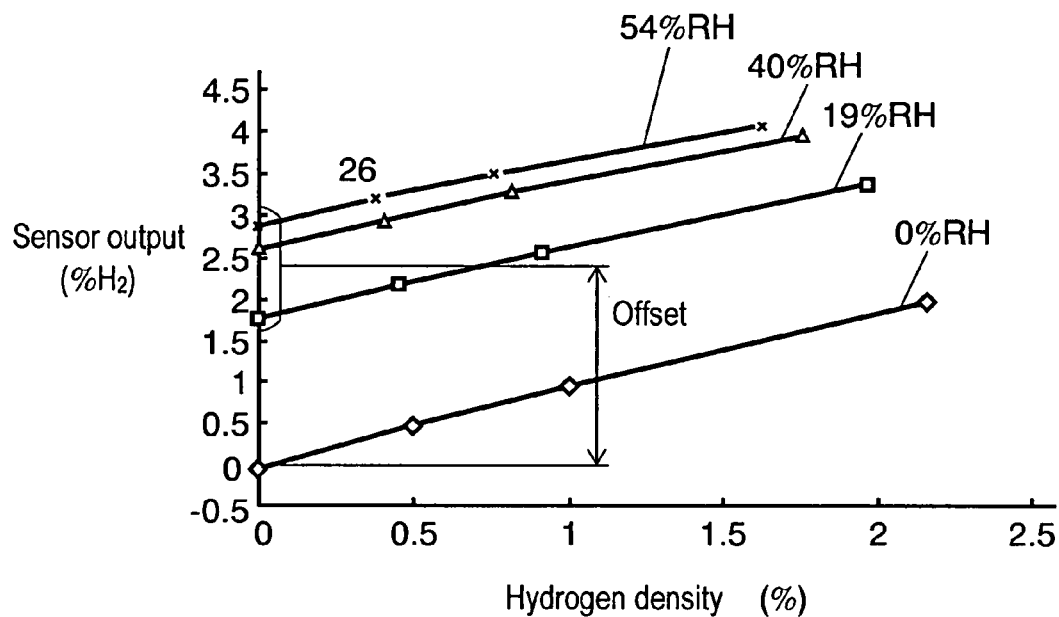
FIG. 11 is a characteristic diagram of hydrogen concentration output of the heater element in FIG. 2.

Here, hydrogen concentration dependence is shown when H value is used as a representative value, at 80° C. in a humidified ambience. Meanwhile, H values output for each hydrogen concentration and humidity are normalized. In other words, H value output when only dry air (0% RH, where RH is relative humidity) is passed through gas sensor 24 is to be zero. Also, H value output when air with 1% of hydrogen mixed is passed through the gas sensor is to be one. FIG. 11, showing the result, is a characteristic diagram of hydrogen concentration output when heater element 1 generates high-temperature heat and the hydrogen is humidified. The horizontal axis shows hydrogen concentration (%) passed through the gas sensor, and the vertical axis shows normalized sensor output (% $H_2$).

FIG. 11 indicates that, if moisture is contained in the ambience, the sensor output changes due to the moisture so largely that it cannot be neglected, and both hydrogen sensing and humidity sensing have the same level of sensitivities. The situation is also the same with L value. Therefore, hydrogen sensing and humidity sensing cannot be performed separately with either L value or H value. Consequently, the gas sensor according to the embodiment outputs both concentrations by performing the calculation shown below.

Generally, the heat conductivity of a gas has temperature dependence, and thus correction for T value, corresponding to an ambient temperature, is made at first for L value and H value. Specifically, zero-point (output for a case where only dry air exists) corrections are made first. Those corrections are made with correcting formulas which are evolved from T values, L values, and H values, which are outputs while dry air is passed through gas sensor 24 at various temperatures. The actual output examples are shown in FIG. 12.

Figure 12:
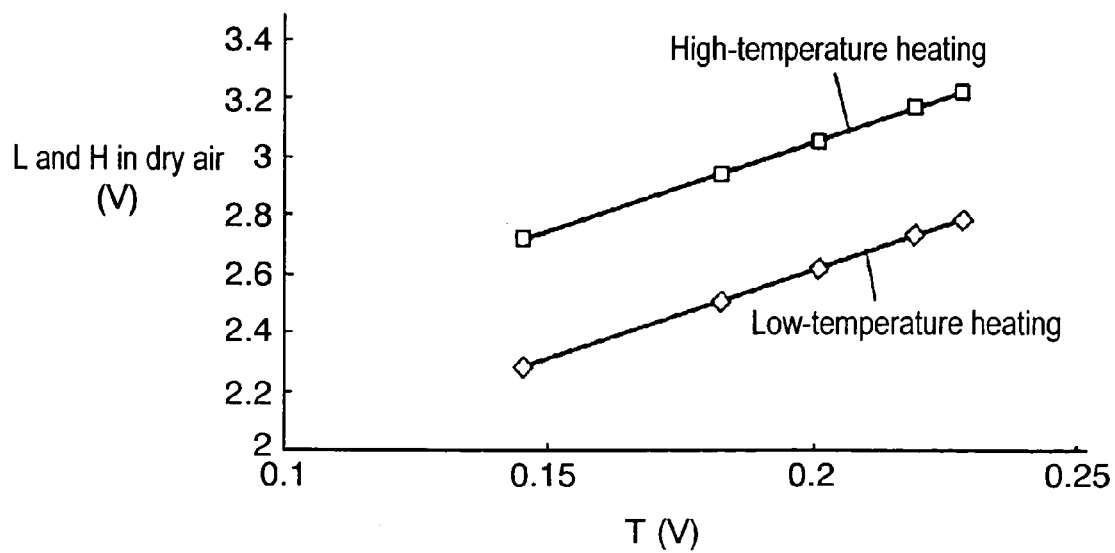
FIG. 12 is a zero-point temperature characteristic diagram of the heater element in FIG. 2.

FIG. 12 shows a result of plotting points in which L values and H values output at ambient temperatures of −40, 20, 50, 80, and 95° C. are indicated with the vertical axis, and T values, corresponding to an ambient temperature, are indicated with the horizontal axis. The graph indicates that both L value and H value change with T value, and the zero-point has temperature dependence. From this result, zero-point correcting formulas for L value and H value are obtained by quadratic approximation with least-square method as follows:

$$L0 = 1.2446 \times T^2 + 5.6767 \times T + 1.436 \quad (1)$$

$$H0 = 1.5997 \times T^2 + 5.5951 \times T + 1.8743 \quad (2)$$

Specifically, for L value and H value output in an environment with certain arbitrary humidity and hydrogen concentration, L0 and H0, which are components influenced by the temperature dependence on the zero-point are obtained by substituting T value corresponding to an ambient temperature into formulas (1) and (2). Therefore, ZL and ZH, which are zero-point-corrected L value and H value output in an arbitrary environment, are obtained by the following formulas. In this way, formulas (1) through (4) are zero-point correcting formulas for correcting L value and H value from T value corresponding to an ambient temperature.

$$ZL = L - L0 \quad (3)$$

$$ZH = H - H0 \quad (4)$$

Here, formulas (1) and (2) adopt quadratic approximation, substantially reducing correction errors compared to linear approximation.

Next, a description is made for sensitivity correction with an ambient temperature. The heat conductivity of a gas generally changes according to an ambient temperature even if a gas with the same concentration exists. In other words, gas sensitivity in heat conductivity has temperature characteristic. Accordingly, corrections are made with correcting formulas which are evolved from T values, L values, and H values, which are outputs while dry air including hydrogen with constant concentration (1%, here) is passed through the gas sensor at various temperatures. In this case, changing the temperature also changes the zero point as aforementioned, and thus L value and H value are sensitivity-corrected for zero-point-corrected values (ZL and ZH) in advance with formulas (3) and (4).

Figure 13:
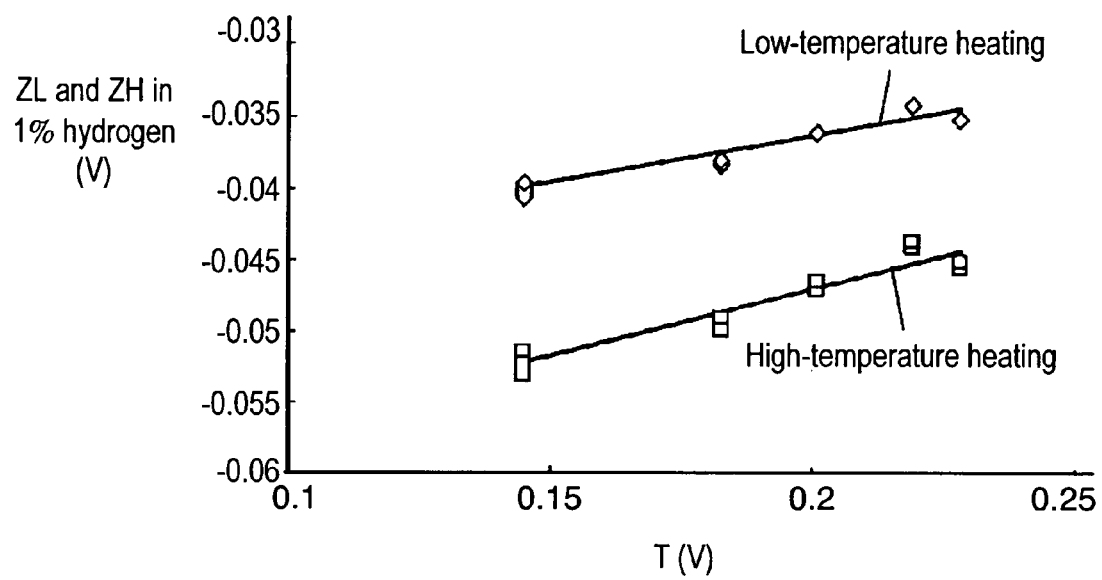
FIG. 13 is a temperature characteristic diagram of zero-point-corrected output of the heater element in FIG. 2.

FIG. 13 shows actual temperature dependence of ZL and ZH, which are output for dry air including 1% hydrogen (i.e. 1% hydrogen sensitivity). The ambient temperature is changed in the same way as in the zero-point correction. In addition, the points are plotted with the horizontal axis as T values (corresponding to an ambient temperature), and with the vertical axis as ZL and ZH, respectively. FIG. 13 indicates that the sensitivity for 1% hydrogen also has temperature dependence. Sensitivity-correcting formulas for ZL and ZH are obtained by quadratic approximation with least-square method as follows:

$$ZL1=0.0627 \times T^2+0.0424 \times T-0.0472 \qquad (5)$$

$$ZH1=0.0996 \times T^2+0.0566 \times T-0.0623 \qquad (6)$$

Here, ZL1 and ZH1 are sensitivity-correcting coefficients by temperature. With these coefficients, KL and KH, which are values of ZL and ZH output in an arbitrary environment, sensitivity-corrected and normalized to hydrogen concentrations, are obtained by the following formulas. In other words, formulas (5) through (8) are sensitivity-correcting formulas for heater element 1 obtained in advance from a concentration-known gas to be sensed.

$$KL=ZL/ZL1 \qquad (7)$$

$$KH=ZH/ZH1 \qquad (8)$$

With formulas (7) and (8), the units for KL (first normalized output) and KH (second normalized output) are normalized to the percentages of hydrogen concentration (hereinafter, abbreviated as % $H_2$). Formulas (5) and (6) also adopt quadratic approximation, reducing correction errors compared to linear approximation in the same way as in zero-point corrections.

Figure 14:
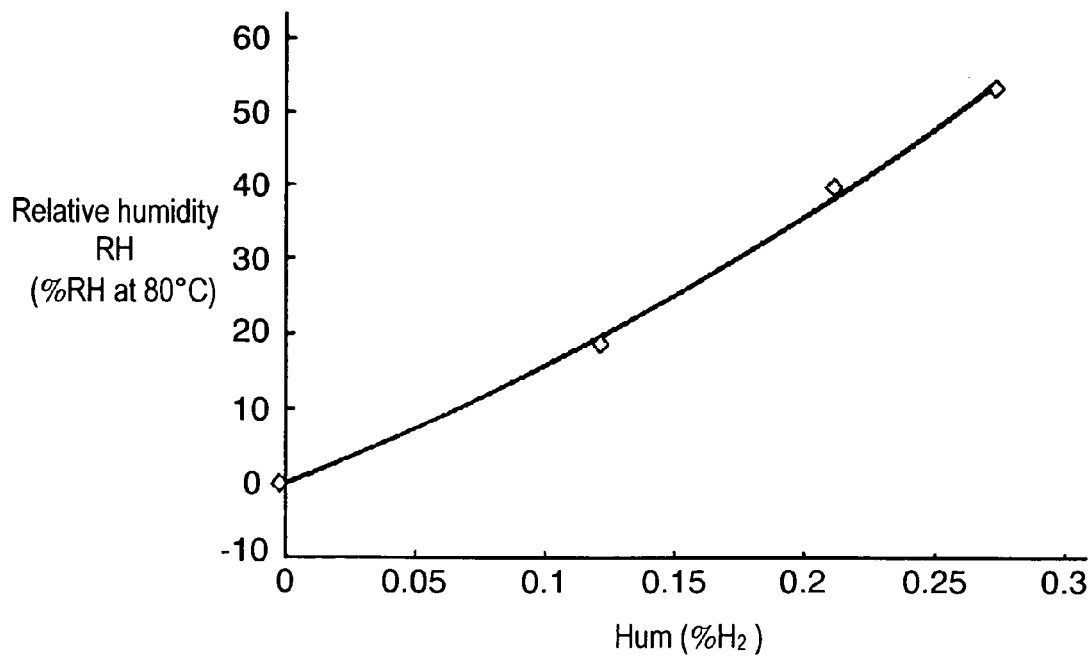
FIG. 14 is a graph of the correlation between corrected output differences when the heater element in FIG. 2 generates heat at a low temperature and a high temperature, and relative humidity at 80° C.

Next, a description is made for a method to obtain humidity output. KL and KH obtained with formulas (7) and (8) are outputs normalized with hydrogen concentration. Consequently, the difference between both of them corresponds to the output in an arbitrary environment with the influence by hydrogen concentration deducted, namely, humidity. This is based on that the influence on both heat conductivities can be approximated as a simple sum, for air with hydrogen and vapor mixed therein, as long as hydrogen is contained up to approximately 4%. In other words, if the hydrogen concentration is within 4%, the output sensitivity of hydrogen concentration is as the same level as that of humidity. In addition, this hydrogen concentration is under explosion limit. Limiting hydrogen concentration to such a range improves the accuracy in correcting calculation, enabling hydrogen leakage to be sensed within a safe concentration range. Further, because hydrogen and humidity sensitivities are different each other, the difference between KL and KH, which are normalized outputs calculated so that the sensitivity for hydrogen concentration becomes equal, is to deduct only hydrogen sensitivity, and the remaining value represents humidity. FIG. 14 shows the result of the plotted correlation between the actual difference and the humidity. The horizontal axis shows the difference "Hum" (=KH−KL), and the vertical axis shows RH, the relative humidity at 80° C. FIG. 14 indicates that the correlation of RH to "Hum", unlike in a conventional technology, does not have a nonlinear characteristic with a peak, but a substantially linear characteristic allowing humidity to be determined uniquely.

The formula (9) shows this correlation quadratic-approximated with least-square method.

$$RH=243.65 \times Hum^2+132.57 \times Hum+0.1011 \qquad (9)$$

Therefore, substituting normalized output difference "Hum" into formula (9) provides humidity RH, where in this embodiment, humidity is obtained as a unit of relative humidity at 80° C. If T value corresponding to an ambient temperature changes, RH is converted to an absolute humidity according to T value using a known formula or the like, or to relative humidity at T value, to obtain humidity at an arbitrary temperature.

Figure 15:
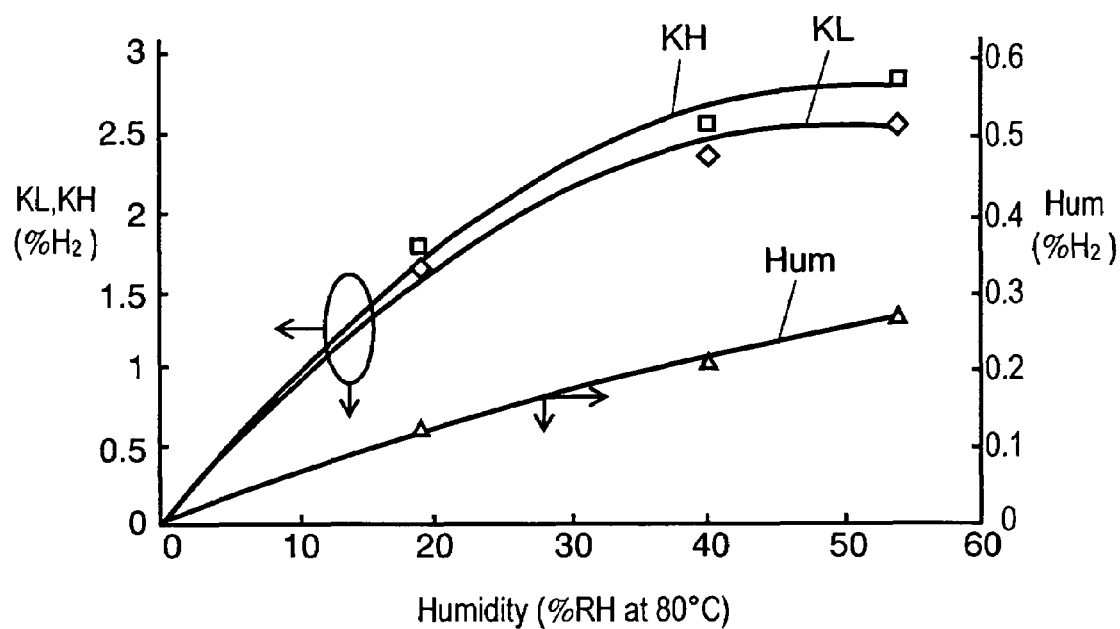
FIG. 15 is a graph of the correlation between zero-point-corrected and sensitivity-corrected output, and relative humidity, for the gas sensor of the embodiment according to the present invention.

Here, a description is made using FIG. 15 for a reason why the characteristic of "Hum" to humidity does not show a nonlinear characteristic with a peak. FIG. 15 is a correlation diagram of KL, KH, and "Hum" to humidity RH in humid air not including hydrogen, where the horizontal axis shows humidity; the left vertical axis, KL and KH; the right vertical axis, "Hum", respectively. FIG. 15 indicates that the characteristics of normalized output KL and KH to humidity are all nonlinear characteristics having a peak. This is because the heat conduction characteristic that humid air has is directly shown. Therefore, approximate formulas for KL and KH to humidity must be expressed with a quadratic equation or one with a higher order. Accordingly, solving simultaneous equations using this approximate formula (estimation equation) like a conventional method brings a plurality of solutions, disabling humidity and eventually hydrogen concentration to be uniquely determined.

However, if the heat conductivity of a mixed gas such as a humid air is calculated with a Sutherland-Wassiljewa-type theoretical formula, heat conductivity changes according to temperature, even for a mixed gas with the same concentration. This is because combination coefficients in the formula, and the heat conductivity of the pure component in the constitutional gas, have temperature characteristic. Therefore, if heating temperatures of the heater element are different, the humidity sensitivities are different each other, even in the same humidity level. This is supported also by the fact that KL is differently plotted from KH in FIG. 15. Focusing attention on this point, when calculating the difference in output (corresponding to KL and KH, here) from the heater element at different heating temperatures using the above-mentioned theoretical formula, it has a substantially linear characteristic in the operating humidity range of the gas sensor. FIG. 15 shows the actual differences (="Hum") between KL and KH. FIG. 15 indicates that "Hum" to humidity RH has a substantially linear characteristic, also supporting the theoretical calculation. From these, while the conventional method cannot uniquely determine humidity, the calculation method according to the present invention can uniquely determine humidity by using formula (9).

Figure 16:
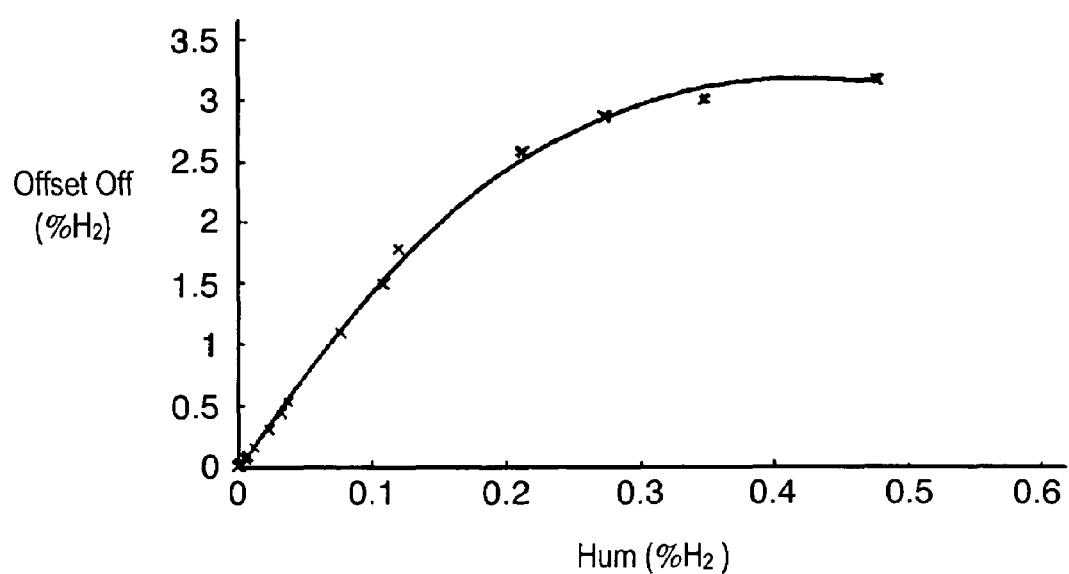
FIG. 16 a graph of the correlation between corrected output differences when the heater element in FIG. 2 generates heat at a low temperature and a high temperature; and offsets.

Next, a description is made for a method to obtain hydrogen concentration. FIG. 11 indicates that humidity correction can be made by deducting an offset according to humidity. Therefore, obtaining the correlation between humidity and the offset enables humidity correction. FIG. 14 indicates that "Hum" and humidity have a linear relation, and thus the correlation between "Hum" and offset "Off" is shown in FIG. 16, where the horizontal axis shows "Hum", and the vertical axis shows "Off" obtained from FIG. 11. FIG. 16 indicates that offset amount "Off", which is to be deducted from "Hum", can be uniquely determined. The calculation formula is shown below that is the correlation between both "Hum" and "Off" cubic-approximated with least-square method. In other words, formulas (10) and (11) are humidity-correcting formulas obtained with a concentration-known gas to be sensed in advance.

$$\text{Off} = 11.247 \times Hum^3 - 27.502 \times Hum^2 + 17.242 \times Hum - 0.0351 \quad (10)$$

Therefore, hydrogen output "Out" after humidity correction is obtained from the following formula.

$$\text{Out} = KH - \text{Off} \quad (11)$$

Formula (10), adopting cubic approximation, reduces correction errors compared to a lower-dimensional approximation.

Figure 17:
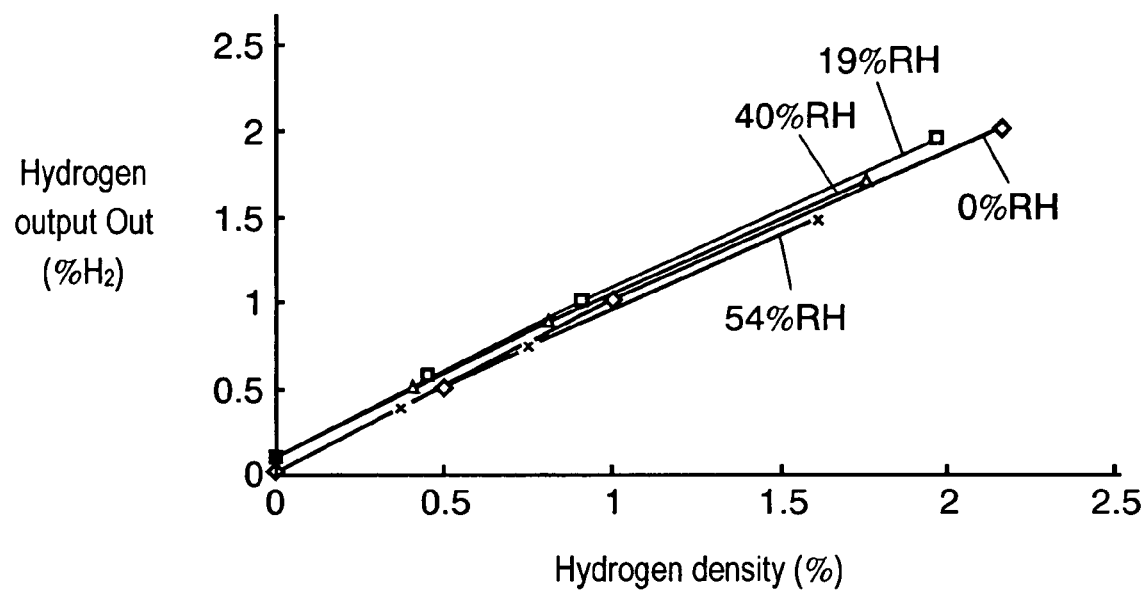
FIG. 17 is a characteristic diagram of the output of humidity-corrected hydrogen concentration under humidity, of the gas sensor of the embodiment according to the present invention.

FIG. 17 shows the actual output in FIG. 11, humidity-corrected with the above-mentioned correction method, where the horizontal axis shows the hydrogen concentration in the gas to be sensed, and the vertical axis shows hydrogen output "Out". FIG. 17 clearly indicates that humidity correction is extremely favorably performed as compared to FIG. 11.

In addition, the calculations shown in formula (11) and earlier are all simple four fundamental operations. Accordingly, compared to calculating simultaneous equations in an order of two or greater as in the conventional method, where a plurality of solutions exist, a gas sensor that is accurate, extremely fast in calculation speed, and responsive, can be implemented. Therefore, for a system to be influenced by humidity, the calculation method in this embodiment is extremely advantageous.

Figure 18:
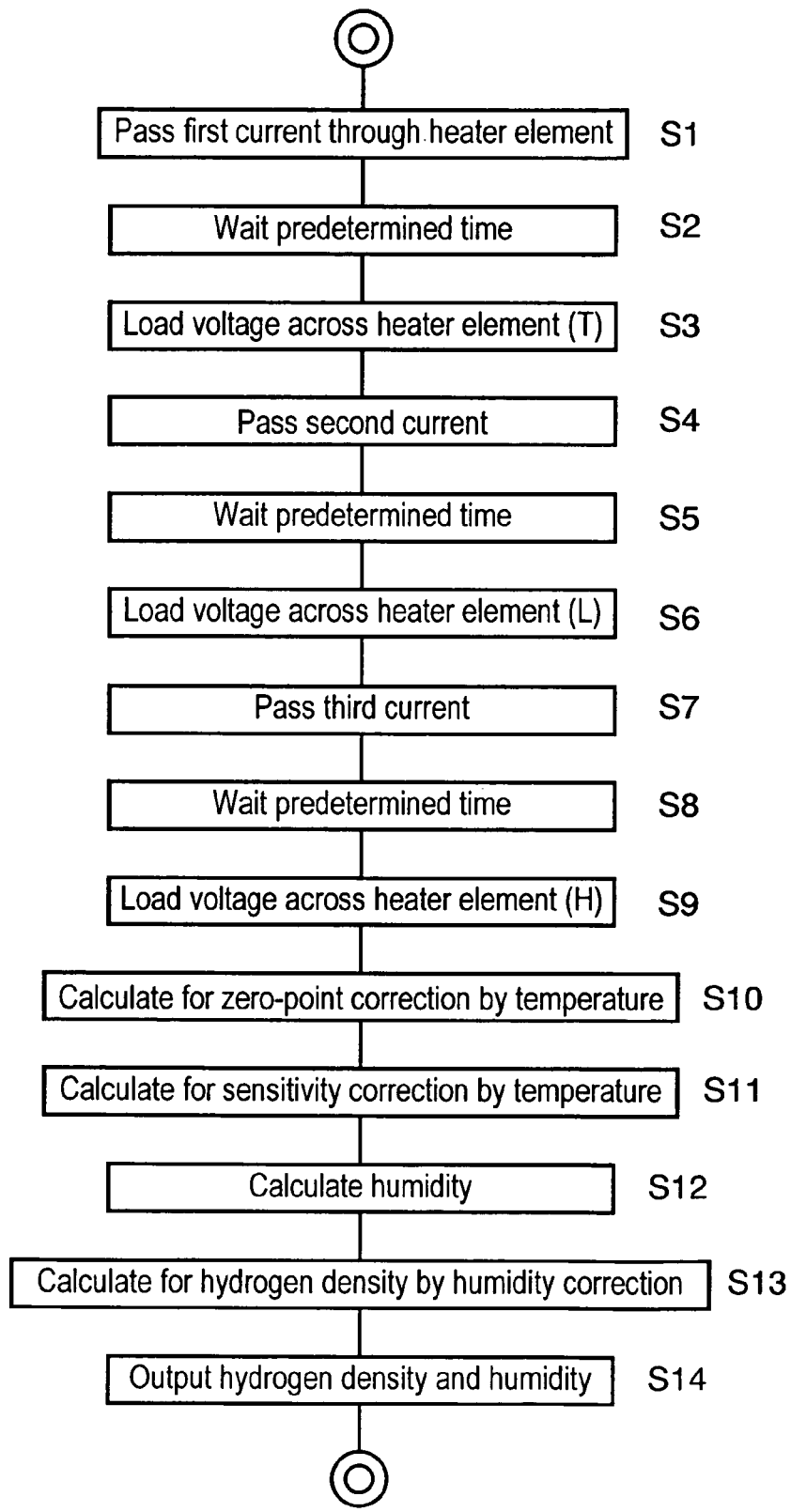
FIG. 18 is a flowchart showing a procedure for calculating hydrogen concentration and humidity of the gas sensor of the embodiment according to the present invention.

The above-mentioned calculation method is programmed in calculator 27. Calculator 27, when T value, L value, and H value are input, which are output from heater element 1 obtained while the gas sensor is operating, performs the calculation for above-mentioned formulas (1) through (11), to output hydrogen and humidity. FIG. 18 shows a flowchart of a subroutine for this calculation procedure.

First, pass the first current (1 mA, here) through the heater element 1 (S1). Next, wait a predetermined time (0.1 second) (S2), and then read T value, a voltage across heater element 1 after a predetermined elapsed time (S3). Next, pass the second current (7 mA, here) through heater element 1 (S4), wait a predetermined time (0.1 second) (S5), and then read L value, a voltage across heater element 1 (S6). In the same way, pass the third current (7.5 mA, here) through heater element 1 (S7), wait a predetermined time (0.1 second) (S8), and then read H value, a voltage across heater element 1 (S9). Next, use formulas (1) through (4) to perform the calculation for zero-point correction by temperature (S10), and then use the result to perform the calculation for sensitivity correction by temperature with formulas (5) through (8) (S11). Next, perform the calculation for humidity using formula (9) (S12), and for hydrogen concentration with humidity correction using formulas (10) and (11) (S13). Finally, output the hydrogen concentration and humidity (S14). Repeat the above-mentioned action as one cycle to continue outputting the hydrogen concentration and humidity. Repeating such sensing operations enables hydrogen concentration and humidity to be monitored with time.

In this embodiment, although only hydrogen concentration and humidity are output, an ambient temperature may be output from T value as required. In addition, although this embodiment describes a case where vapor and hydrogen coexist, also for a combination with a gas other than hydrogen, the concentration of the gas can be output in the same way.

INDUSTRIAL APPLICABILITY

As mentioned above, a gas sensor according to the present invention includes a heater element that contacts a gas to be sensed, mixed in the atmospheric air containing moisture; a power supply unit for supplying the heater element with a current; and a voltmeter for measuring a voltage across the heater element. The gas sensor further includes a calculator for calculating and outputting the humidity and concentration of a gas to be sensed from output voltages of the voltmeter. The calculator supplies the heater element with at least three levels of current, stepwise and continuously for a predetermined time, using the power supply unit. Then, the calculator loads voltages across the heater element after a predetermined elapsed time for the respective current values, and calculates the temperature from the voltage across the heater element for the minimum amount of current. From a zero-point correcting formula and a sensitivity-correcting formula, obtained in advance with the temperature and a concentration-known gas to be sensed, the calculator corrects the voltages across the heater element when passing a current other than the above-mentioned minimum current, to obtain respective normalized outputs. From the difference in these normalized outputs, the calculator calculates humidity, and corrects the normalized outputs with the humidity and a humidity-correcting formula, obtained in advance with a concentration-known gas to be sensed, to obtain the concentration of the gas to be sensed. In such a way, the gas sensor outputs humidity and the concentration of a gas to be sensed. Accordingly, the present invention provides a gas sensor that can sense a gas well accurately by distinguishing the concentration of the gas and the humidity each other even if the gas contains moisture. It is suitable to use the gas sensor to sense hydrogen concentration for a fuel cell system and an automobile with a fuel cell mounted thereon.

The invention claimed is:

1. A gas sensor comprising:
   a heater element for contacting gas to be sensed, the gas being mixed with atmospheric air including moisture;
   a power supply unit for passing current through the heater element;
   a voltmeter for measuring a voltage across the heater element; and
   a calculator for calculating and outputting humidity and concentration of the gas to be sensed, wherein the calculator:
   A) controls the power supply unit, and applies to the heater element current with at least a first value, a second value, and a third value, sequentially, stepwise, and continuously for a predetermined time, the second and third values being greater than the first value,
   B) loads a first output, a second output, and a third output, which are voltages across the heater element, after a predetermined elapsed time, for the first value, the second value, and the third value, respectively, from the voltmeter,
   C) obtains an ambient temperature from the first output,
   D) corrects the second output and the third output using correcting formulas for correcting the second output and the third output, with the ambient temperature obtained, and a zero-point output from the voltmeter when only dry air exists; and correcting formulas for sensitivity of the heater element, obtained in advance from the gas to be sensed with a known concentration; and then obtains a first normalized output for the second value, and a second normalized output for the third value, E) obtains the humidity from a difference between the first normalized output and the second normalized output, and F) obtains the concentration of the gas to be sensed by correcting at least one of the first normalized output and the second normalized output, with the obtained humidity and a correcting formula for humidity, obtained in advance from the gas to be sensed with a known concentration.

2. The gas sensor as claimed in claim 1, wherein the calculator repeats the processes A through F.

3. The gas sensor as claimed in claim 1, wherein the gas to be sensed is hydrogen with a concentration up to 4%.

4. The gas sensor as claimed in claim 1, wherein the first value is within a range in which the heater element hardly generates heat.

5. The gas sensor as claimed in claim 1, wherein the third value is greater than the second value; and wherein the first value, the second value, and the third value are applied to the heater element in this order sequentially.

6. The gas sensor as claimed in claim 1, wherein the heater element includes:
a pedestal made of silicon;
an insulating layer formed on the pedestal; and
a heat generator formed on the insulating layer,
wherein the pedestal is provided with a dent under the insulating layer having the heat generator.

7. The gas sensor as claimed in claim 6, wherein thickness of a part of the heater element, on which the dent is provided, is at least 3 micrometers but at most 10 micrometers.

8. The gas sensor as claimed in claim 6, wherein the insulating layer is made of silica.

9. The gas sensor as claimed in claim 6, wherein the heater element further includes a protective layer formed on the heat generator.

10. The gas sensor as claimed in claim 9, wherein the protective layer is made of silica.

11. The gas sensor as claimed in claim 6, wherein the heater element is provided with a through-hole between the heat generator and the pedestal.

12. The gas sensor as claimed in claim 6, wherein the heater element has a winding part provided with at least the heat generator.

13. The gas sensor as claimed in claim 1, wherein the heater element has a platinum thin-film.

14. The gas sensor as claimed in claim 1, further comprising:
a first can arranged at an outside of the heater element, and provided with a first hole; and
a second can arranged at an outside of the first can, and provided with a second hole,
wherein the first hole and the second hole are displaced from each other.

15. The gas sensor as claimed in claim 14, wherein at least either of the first can and the second can is black.

16. The gas sensor as claimed in claim 14, further comprising:
at least one of a first net covering the first hole, made of metal, and a second net covering the second hole, made of metal.

17. The gas sensor as claimed in claim 16, wherein at least one of the first net and the second net is black.

18. A fuel cell system comprising:
a gas sensor for outputting hydrogen concentration;
a fuel cell for generating electric power using hydrogen as a fuel; and
a control circuit for stopping supply of the fuel cell with hydrogen when output for hydrogen from the gas sensor exceeds a predetermined value,
wherein the gas sensor comprises:
a heater element for contacting gas to be sensed, the gas being mixed with atmospheric air including moisture;
a power supply unit for passing current through the heater element;
a voltmeter for measuring a voltage across the heater element; and
a calculator for calculating and outputting humidity and concentration of the gas to be sensed, wherein the calculator;
A) controls the power supply unit, and applies to the heater element current with at least a first value, a second value, and a third value, sequentially, stepwise, and continuously for a predetermined time, the second and third values being greater than the first value,
B) loads a first output, a second output, and a third output, which are voltages across the heater element, after a predetermined elapsed time, for the first value, the second value, and the third value, respectively, from the voltmeter,
C) obtains an ambient temperature from the first output,
D) corrects the second output and the third output using correcting formulas for correcting the second output and the third output, with the ambient temperature obtained, and a zero-point output from the voltmeter when only dry air exists; and correcting formulas for sensitivity of the heater element, obtained in advance from the gas to be sensed with a known concentration, and then obtains a first normalized output for the second value, and a second normalized output for the third value,
E) obtains the humidity from a difference between the first normalized output and the second normalized output, and
F) obtains the concentration of the gas to be sensed by correcting at least one of the first normalized output and the second normalized output, with the obtained humidity and a correcting formula for humidity, obtained in advance from the gas to be sensed with a known concentration.

19. The fuel cell system as claimed in claim 18, further comprising:
a duct for supplying the fuel cell with hydrogen; and
a ventilator for ventilating a space including the duct,
wherein the control circuit controls the ventilator to ventilate the space, when output for hydrogen from the gas sensor exceeds a predetermined value.

20. An automobile comprising:
a main body for forming a cabin space;
a tire for supporting the main body;
a motor for driving the tire;
a fuel cell for generating power using hydrogen as a fuel to provide the motor with power;

a gas sensor for outputting hydrogen concentration, arranged on an upper part of the cabin space; and a control circuit for stopping supply of the fuel cell with hydrogen when output for hydrogen from the gas sensor exceeds a predetermined value, wherein the gas sensor comprises:

a heater element for contacting gas to be sensed, the gas being mixed with atmospheric air including moisture;

a power supply unit for passing current through the heater element;

a voltmeter for measuring a voltage across the heater element; and a calculator for calculating and outputting humidity and concentration of the gas to be sensed, wherein the calculator;

A) controls the power supply unit, and applies to the heater element current with at least a first value, a second value, and a third value, sequentially, step-wise, and continuously for a predetermined time, the second and third values being greater than the first value, B) loads a first output, a second output, and a third output, which are voltages across the heater element, after a predetermined elapsed time, for the first value, the second value, and the third value, respectively, from the voltmeter, C) obtains an ambient temperature from the first output, D) corrects the second output and the third output using correcting formulas for correcting the second output and the third output, with the ambient temperature obtained, and a zero-point output from the voltmeter when only dry air exists; and correcting formulas for sensitivity of the heater element, obtained in advance from the gas to be sensed with a known concentration, and then obtains a first normalized output for the second value, and a second normalized output for the third value, E) obtains the humidity from a difference between the first normalized output and the second normalized output, and F) obtains the concentration of the gas to be sensed by correcting at least one of the first normalized output and the second normalized output, with the obtained humidity and a correcting formula for humidity, obtained in advance from the gas to be sensed with a known concentration.

21. The automobile as claimed in claim 20, further comprising:

a ventilator for ventilating a space in the main body, by controlling the control circuit, when output for hydrogen from the gas sensor exceeds a predetermined value.

22. The automobile as claimed in claim 20, further comprising:

an annunciator for alarming, by controlling the control circuit, when output for hydrogen from the gas sensor exceeds a predetermined value.

23. The automobile as claimed in claim 20, further comprising an air conditioner for conditioning humidity in the cabin space, wherein the control circuit controls the air conditioner, based on humidity output from the gas sensor, so that the cabin space has an optimum humidity.

24. The automobile as claimed in claim 20, wherein the gas sensor always outputs hydrogen concentration and humidity.

25. A method of obtaining humidity and concentration of gas to be sensed, using a heater element contacting the gas to be sensed, mixed with atmospheric air including moisture, the method comprising the steps of:

A) applying to the heater element current of at least a first value, a second value, and a third value, sequentially, stepwise, and continuously for a predetermined time, the second and third values being greater than the first value, B) loading a first output, a second output, and a third output, which are voltages across the heater element, after a predetermined elapsed time, for the first value, the second value, and the third value, respectively, C) obtaining an ambient temperature from the first output, D) correcting the second output and the third output using correcting formulas for correcting the second output and the third output, with the ambient temperature obtained, and a zero-point output from the voltmeter when only dry air exists; and correcting formulas for sensitivity of the heater element, obtained in advance from the gas to be sensed with a known concentration, and then obtaining a first normalized output for the second value, and a second normalized output for the third value, E) obtaining the humidity from a difference between the first normalized output and the second normalized output, and F) obtaining the concentration of the gas to be sensed by correcting at least one of the first normalized output and the second normalized output, with the obtained humidity, and a correcting formula for humidity, obtained in advance from the gas to be sensed with a known concentration.

* * * * *